(12) United States Patent
Isobe et al.

(10) Patent No.: US 8,794,100 B2
(45) Date of Patent: Aug. 5, 2014

(54) REMOTE-CONTROLLED ACTUATOR

(71) Applicant: NTN Corporation, Osaka (JP)

(72) Inventors: Hiroshi Isobe, Iwata (JP); Takayoshi Ozaki, Iwata (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 14/045,387

(22) Filed: Oct. 3, 2013

(65) Prior Publication Data

US 2014/0026704 A1    Jan. 30, 2014

Related U.S. Application Data

(60) Division of application No. 13/200,942, filed on Oct. 5, 2011, now Pat. No. 8,573,090, which is a continuation of application No. PCT/JP2010/056304, filed on Apr. 7, 2010.

(30) Foreign Application Priority Data

Apr. 15, 2009   (JP) ................................ 2009-098715

(51) Int. Cl.
    *B25J 13/00*    (2006.01)
(52) U.S. Cl.
    USPC .............. 74/490.04; 901/21; 606/79; 606/81; 606/89
(58) Field of Classification Search
    CPC ..................... A61B 17/32002; A61B 17/1631; A61B 17/1633; A61B 17/1642; A61B 2017/1651; A61B 2017/00477; A61B 2017/2927; A61B 2017/2904; A61B 17/1668; A61B 19/2203; A61B 19/22; A61B 17/2909; A61B 2017/16; B25J 13/00
    USPC ................ 74/490.01–490.04; 901/21, 31, 41; 606/79, 81, 86 R, 87, 89, 96; 277/304, 277/431, 432
    See application file for complete search history.

(56) References Cited

U.S. PATENT DOCUMENTS 550,783 A   *  12/1895  Elliot .............................. 175/75
RE13,884 E  *  2/1915   Herzmark ...................... 74/502
(Continued)

FOREIGN PATENT DOCUMENTS

DE      4421658 A1    1/1995
JP      6-315486      11/1994
(Continued)

OTHER PUBLICATIONS

International Search Report for PCT/JP2010/056304, mailed May 11, 2010.

(Continued)

*Primary Examiner* — Troy Chambers
*Assistant Examiner* — Valentin Craciun

(57) ABSTRACT

A remote controlled actuator includes a spindle for holding a tool, a spindle guide section of an elongated configuration, a distal end member rotatably supporting the spindle, and a drive unit housing connected to a base end of the spindle guide section. The distal end member is fitted to the spindle guide section for alteration in attitude. The spindle guide section includes an outer shell pipe, a rotary shaft, and guide pipe. Within the guide pipe, an attitude altering member is inserted to alter the attitude of the distal end member. A connection device detachably connects the spindle guide section with the drive unit housing.

11 Claims, 12 Drawing Sheets

(56) References Cited

U.S. PATENT DOCUMENTS

| | | | |
|---|---|---|---|
| 3,617,143 A * | 11/1971 | McKee | 408/127 |
| 4,265,231 A | 5/1981 | Scheller, Jr. et al. | |
| 4,466,429 A | 8/1984 | Loscher et al. | |
| 5,356,064 A * | 10/1994 | Green et al. | 227/177.1 |
| 5,478,093 A | 12/1995 | Eibl et al. | |
| 5,509,918 A * | 4/1996 | Romano | 606/80 |
| 5,569,254 A * | 10/1996 | Carlson et al. | 606/79 |
| 5,662,666 A * | 9/1997 | Onuki et al. | 606/148 |
| 5,700,265 A * | 12/1997 | Romano | 606/80 |
| 7,204,844 B2 * | 4/2007 | Jensen et al. | 606/205 |
| 7,549,992 B2 * | 6/2009 | Shores et al. | 606/79 |
| 7,585,300 B2 * | 9/2009 | Cha | 606/80 |
| 7,922,720 B2 * | 4/2011 | May et al. | 606/80 |
| 8,083,765 B2 * | 12/2011 | Lee et al. | 606/205 |
| 8,156,840 B2 * | 4/2012 | Tange | 74/490.03 |
| 8,161,838 B2 * | 4/2012 | Duval | 74/490.04 |
| 2002/0111635 A1 | 8/2002 | Jensen et al. | 606/130 |
| 2003/0000774 A1 | 1/2003 | Highley | |
| 2003/0030225 A1 * | 2/2003 | Uesugi et al. | 277/431 |
| 2003/0130648 A1 * | 7/2003 | Jensen et al. | 606/1 |
| 2003/0225364 A1 * | 12/2003 | Kraft et al. | 604/35 |
| 2004/0122460 A1 | 6/2004 | Shores et al. | |
| 2005/0165420 A1 * | 7/2005 | Cha | 606/150 |
| 2005/0192595 A1 * | 9/2005 | Green et al. | 606/130 |
| 2005/0273086 A1 * | 12/2005 | Green et al. | 606/1 |
| 2006/0178672 A1 * | 8/2006 | Shores et al. | 606/79 |
| 2006/0229624 A1 * | 10/2006 | May et al. | 606/79 |
| 2007/0258782 A1 | 11/2007 | Miyata et al. | |
| 2007/0265653 A1 | 11/2007 | Suzuki | |
| 2010/0154578 A1 * | 6/2010 | Duval | 74/479.01 |
| 2011/0118544 A1 * | 5/2011 | Adams et al. | 600/104 |
| 2011/0152867 A1 | 6/2011 | Petrzelka et al. | |
| 2012/0010464 A1 * | 1/2012 | Adams et al. | 600/104 |
| 2012/0174694 A1 * | 7/2012 | Duval | 74/490.04 |

FOREIGN PATENT DOCUMENTS

| | | |
|---|---|---|
| JP | 2001-17446 | 1/2001 |
| JP | 2002-518067 | 6/2002 |
| JP | 2005-516662 | 6/2005 |
| JP | 2005-528159 | 9/2005 |
| JP | 2007-68636 | 3/2007 |
| JP | 2007-301149 | 11/2007 |
| WO | 99/63891 A1 | 12/1999 |
| WO | 03/065906 A2 | 8/2003 |
| WO | 03/101308 A1 | 12/2003 |

OTHER PUBLICATIONS

Japanese Office Action issued Jul. 2, 2013 in corresponding Japanese Application No. 2009-098715.
International Preliminary Report on Patentability mailed Nov. 24, 2011 issued in corresponding International Patent Application No. PCT/JP2010/056304.
U.S. Office Action issued Nov. 29, 2012 in copending U.S. Appl. No. 13/200,942.
U.S. Office Action issued Mar. 22, 2013 in copending U.S. Appl. No. 13/200,942.
U.S. Notice of Allowance issued Sep. 4, 2013 in copending U.S. Appl. No. 13/200,942.
U.S. Appl. No. 13/200,942, filed Oct. 5, 2011, Hiroshi Isobe, NTN Corporation, Jan. 9, 2014.
Extended European Search Report issued Oct. 2, 2013 in corresponding European Application No. 10764382.7.

* cited by examiner

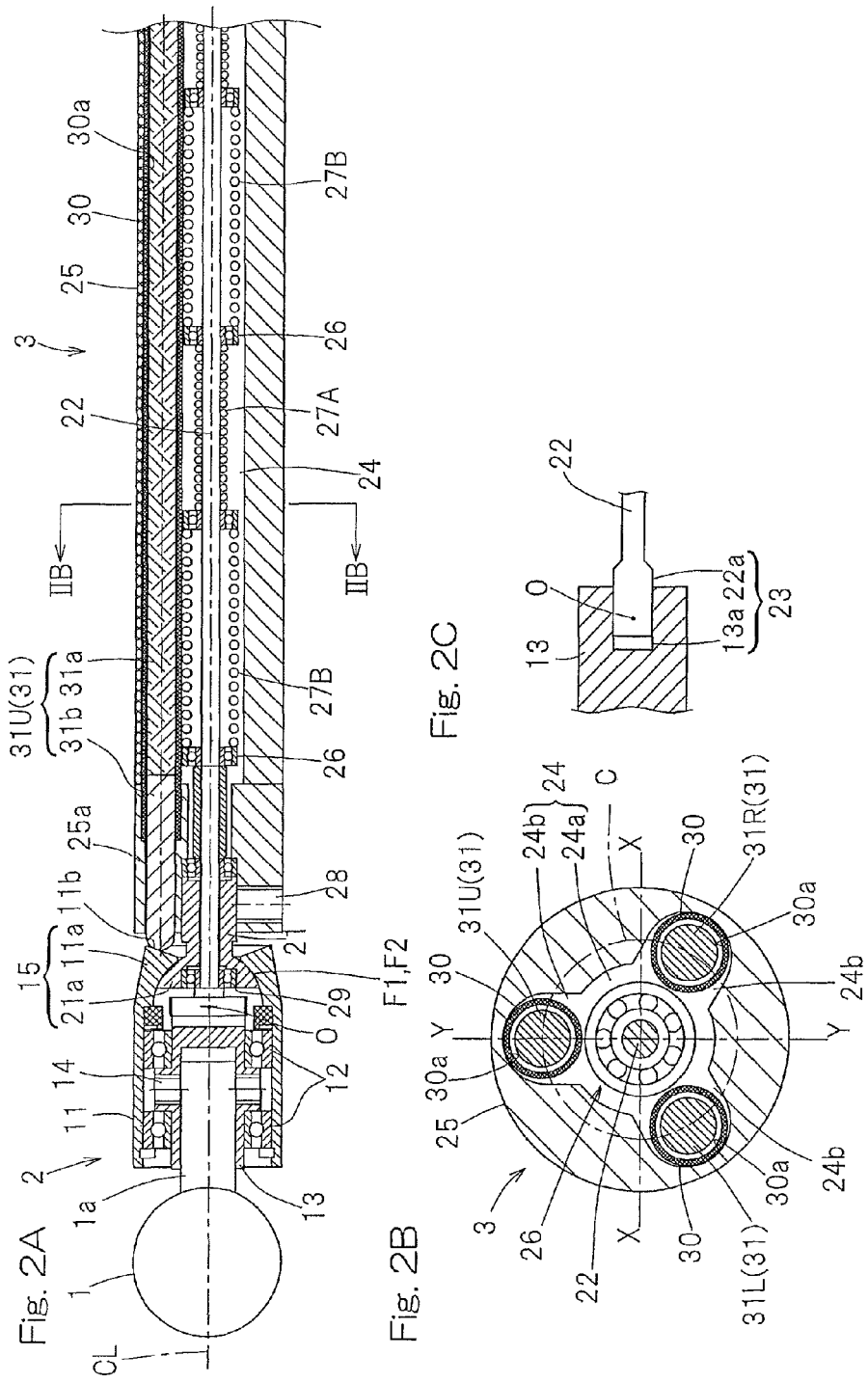

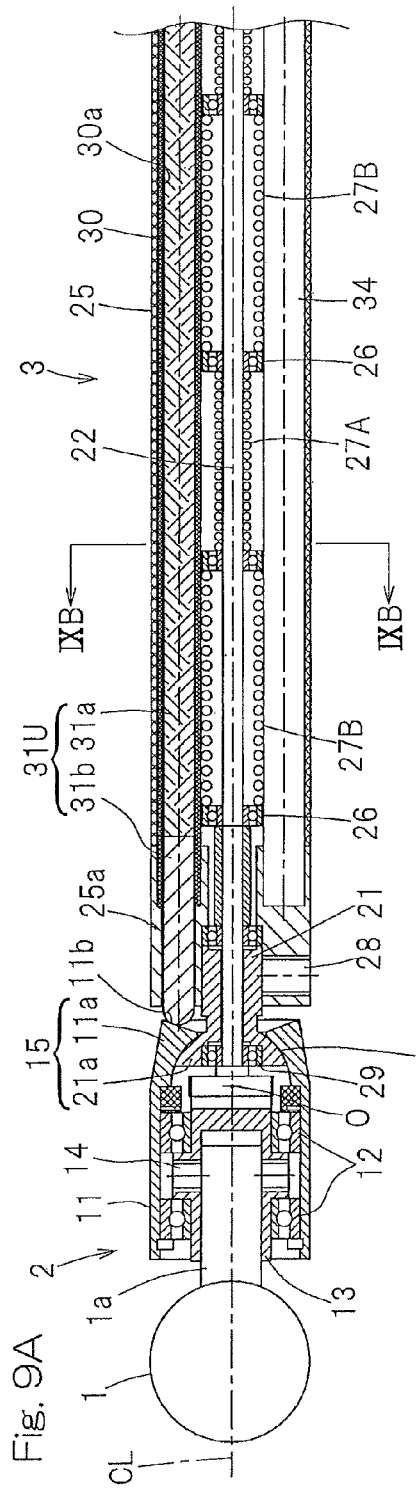
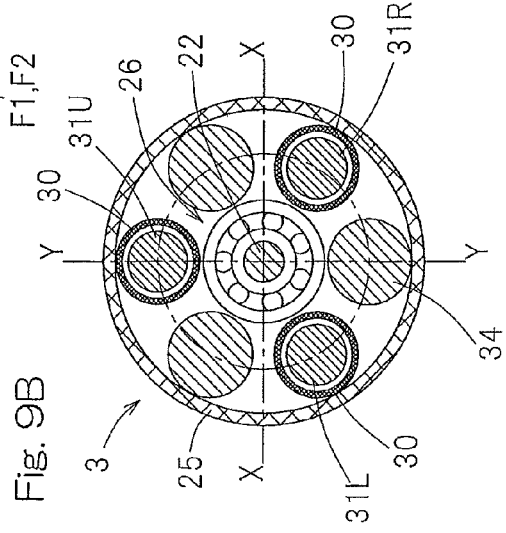
Fig. 9A
Fig. 9B

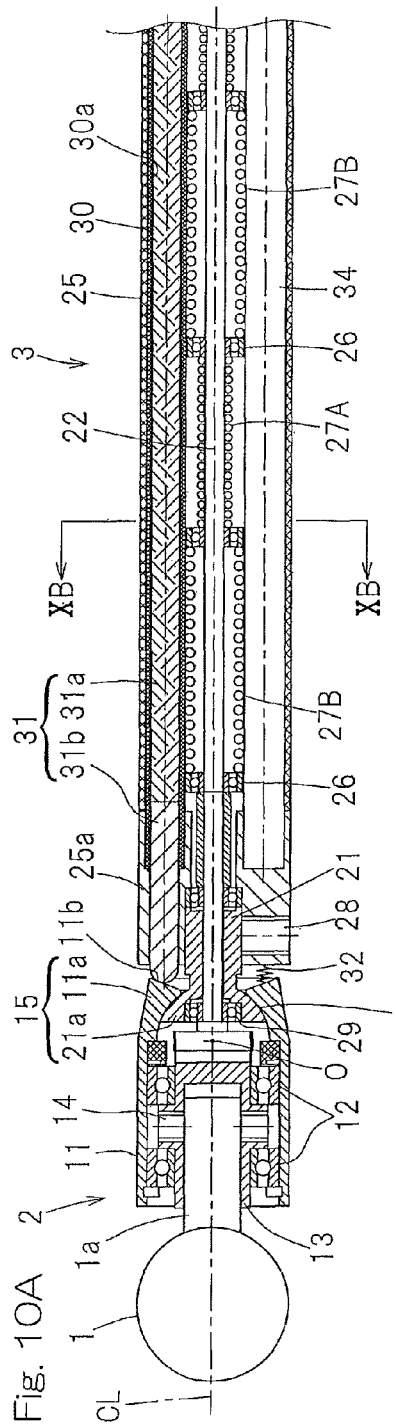
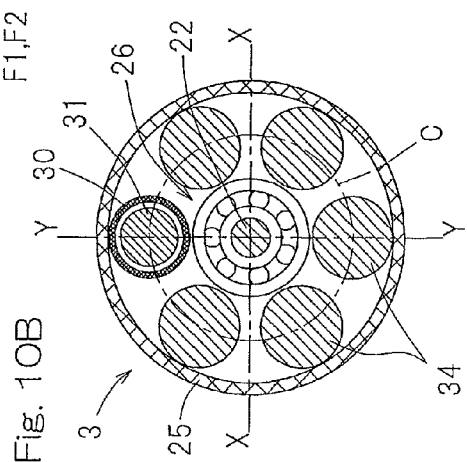
Fig. 10A
Fig. 10B

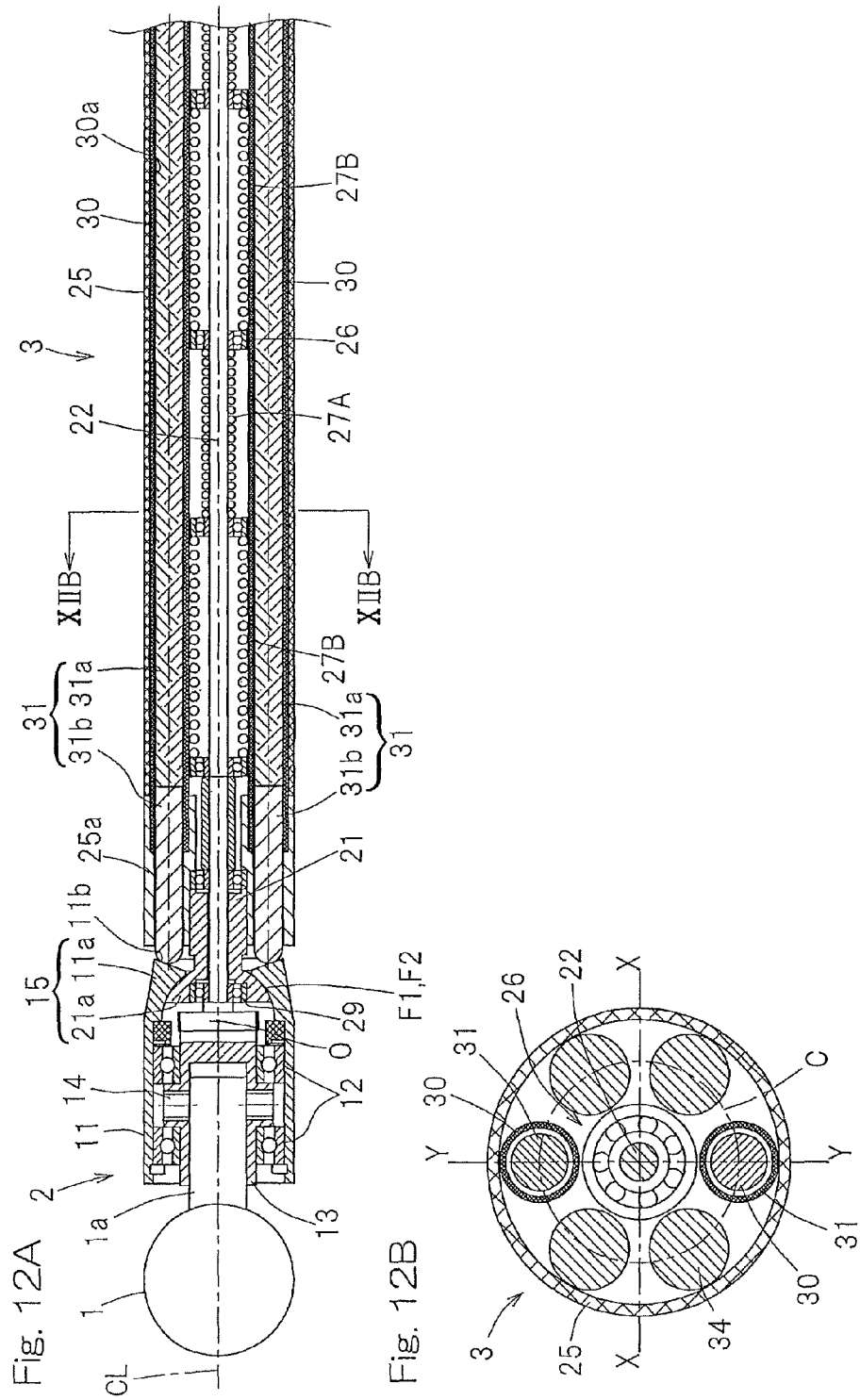

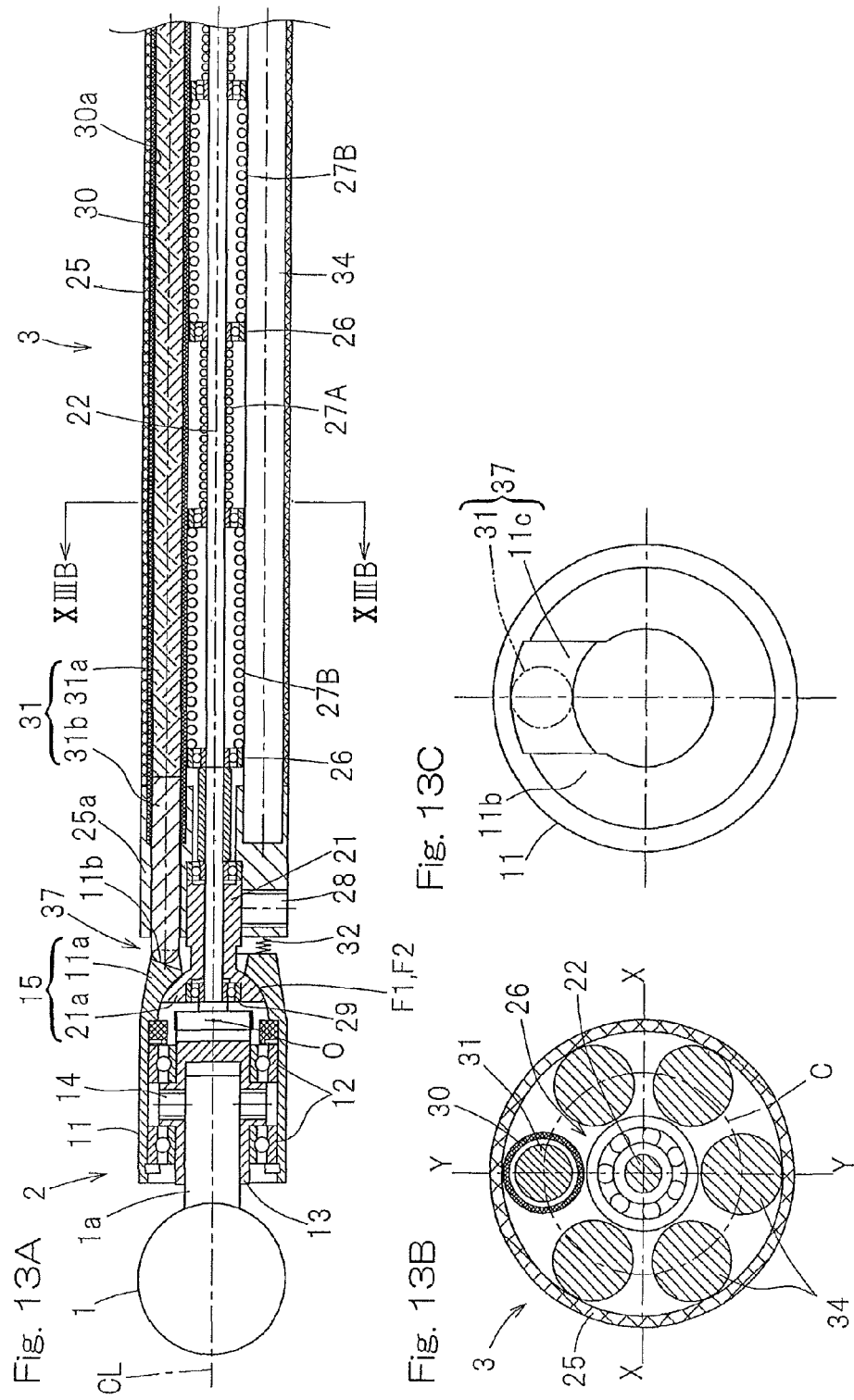

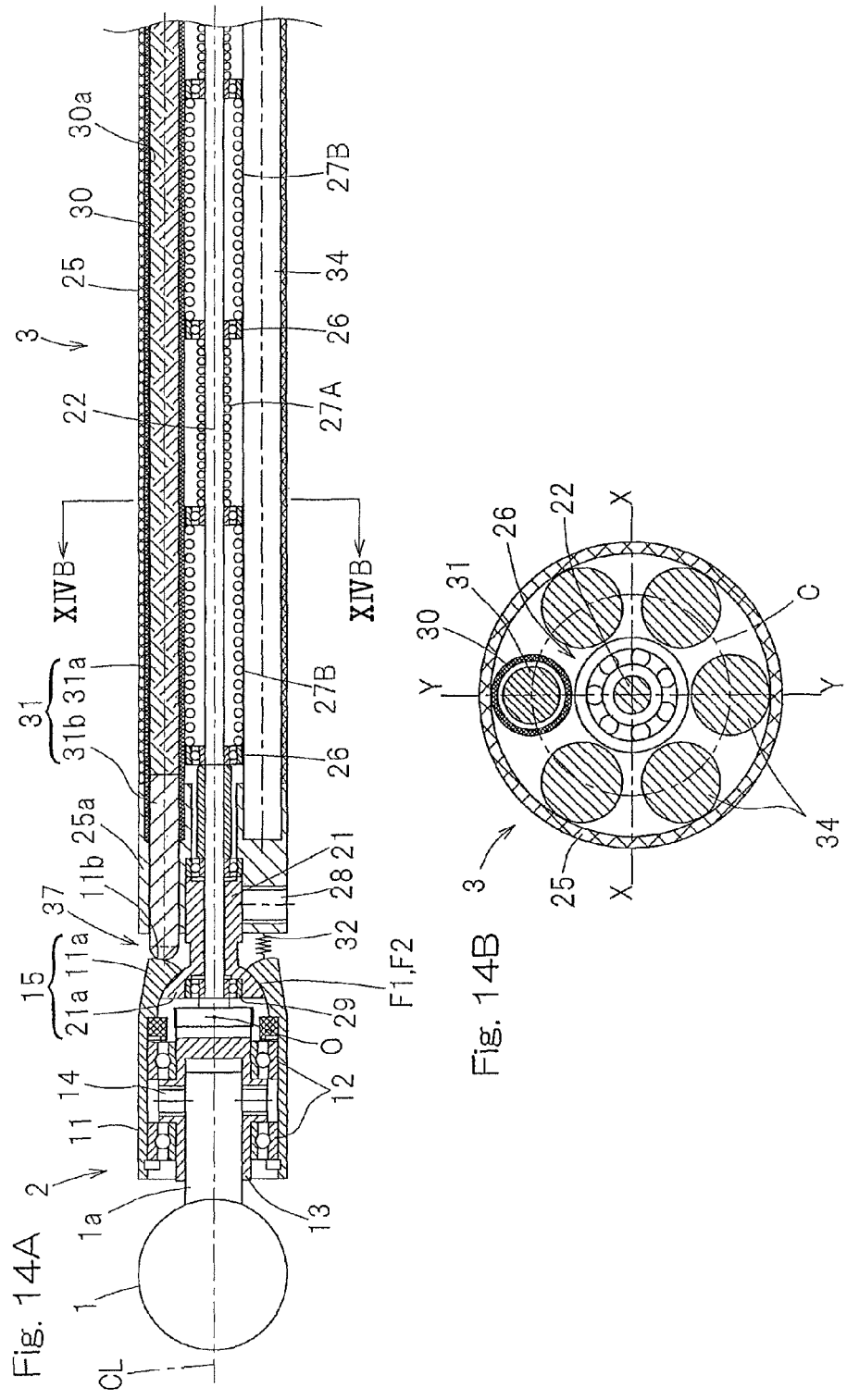

REMOTE-CONTROLLED ACTUATOR

CROSS-REFERENCE TO RELATED APPLICATIONS

This application is a divisional of U.S. patent application Ser. No. 13/200,942, filed on Oct. 5, 2011, which issued as U.S. Pat. No. 8,573,090 on Nov. 5, 2013, which was a continuation application under 35 U.S.C §111(a) of International Application No. PCT/JP2010/056304, filed Apr. 7, 2010, which claims priority to a-Japanese Patent Application No. 2009-098715, filed Apr. 15, 2009, the entire disclosures of which are herein incorporated by reference.

BACKGROUND

1. Field

The present invention relates to a remote controlled actuator for use in medical and machine processing fields and capable of changing the attitude of a machine tool.

2. Description of the Related Art

Remote controlled actuators are currently available; some are used in the medical field for osteal treatment and some are used in the mechanical processing field for drilling and cutting. Any of those remote controlled actuators controls by remote control a machine tool fitted to a distal end of an elongated pipe of a linear or curved configuration. However, since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip joint replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, Japanese Patent Publication No. 2007-301149) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet this desire, the following technique has hitherto been suggested. For example, U.S. Pat. No. 4,466,429 discloses the elongated pipe having its intermediate portion curved twice to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the U.S. Pat. No. 4,265,231 discloses the elongated pipe rotated by 180°.

If in a condition, in which the artificial joint is inserted into an artificial joint insertion hole formed in the living bone, a large gap exists between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever shape the pipe takes, the working range of the tool is limited by the shape of the pipe and, therefore, it is difficult to process the artificial joint insertion hole so that the living bone and the artificial joint may have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

It is to be noted that in the case of the medical actuator having no elongated pipe used therein, a portion where the tool is mounted can change its attitude relative to a portion to be gripped by hand (See, for example, Japanese Patent Publication No. 2001-017446), but nothing has yet been suggested in the art that the attitude of the tool can be altered by remote control.

SUMMARY

In view of the foregoing, the present invention has attempted to provide a remote controlled actuator of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe. It has, however, been found that since the tool is connected to the distal end of the elongated pipe, disposition of a mechanism for changing the attitude of the tool is considerably limited and, therefore, artifices are required to overcome those limitations.

For the surgery operation for artificial joint replacement, for instance, it is desirable to prepare a plurality of straight pipes and curved pipes with various curve configurations and to select among them a pipe with an optimal shape to conform to the shape of the bone of a patient which is an object to be cut. In the case of a construction in which a pipe and a drive unit containing, for example, a rotary drive source are integrated with each other, such a selective use of a plurality of pipes will inevitably lead to the simultaneous exchange of the pipe and the drive unit with good conformation to the shape of the object to be cut. Also, with a medical actuator used in a surgical instrument for the surgery operation for artificial joint replacement, its pipe needs to be sterilized as it is inserted into a patient's body. In the case of the construction in which the pipe section and the drive unit containing, for example, the rotary drive source are integrated with each other, its main body needs to have a complete sealing structure in order to prevent the inside electronic components from failing during the sterilization procedures, thereby resulting in a complicated structure. For these reasons, it is desired that the pipe section and the drive unit can be easily detached from and coupled with each other.

An object of the present invention is to provide a remote controlled actuator that can alter the attitude of a tool provided at a tip end of an elongated pipe and that also allows a simple exchange of a spindle guide section formed as such a pipe as well as exclusive treatments or modifications to the spindle guide section.

A remote controlled actuator according to the present invention includes a spindle guide section of an elongated configuration, a distal end member fitted to a tip end of the spindle guide section through a distal end member connecting unit for alteration in attitude, and a drive unit housing to which a base end of the spindle guide section is connected. The distal end member rotatably supports a spindle for holding a tool. The spindle guide section includes a rotary shaft for transmitting rotation of a tool rotating drive source, provided within the drive unit housing, to the spindle, a guide hole so as to extend to opposite ends thereof, and an attitude altering member reciprocally movably inserted within the guide hole for altering the attitude of the distal end member. The attitude altering member is, while a tip end thereof is held in contact with the distal end member, selectively advanced or retracted one at a time. An attitude altering drive source for selectively advancing or retracting the attitude altering member is provided within the drive unit housing. A connection device is provided for detachably connecting the spindle guide section with the drive unit housing.

According to the above described construction, as a result of rotation of the tool fitted to the distal end member, cutting of the bone or the like takes place. In such case, when the attitude altering member is selectively advanced and retracted one at a time by the attitude altering drive source, the tip end of the attitude altering member works on the distal end member to allow the attitude of the distal end member, fitted to the tip end of the spindle guide section through the distal end member connecting unit for alteration in attitude, to alter. The attitude altering drive source is provided within the drive unit housing on the base end side of the spindle guide section and the alteration of the attitude of the distal end member is carried out by remote control. Since the attitude altering member is passed through the guide hole, the attitude altering member can work on the distal end member properly at all time without being displaced in a direction transverse to the longitudinal direction thereof, and the operation to alter the attitude of the distal end member takes place accurately.

Since the connection device detachably connects the spindle guide section with the drive unit housing, spindle guide sections with various configurations can selectively be mounted to a single drive unit housing to achieve good conformation of so selected spindle guide section to the shape of an object to be cut. Furthermore, the easy detachment of the spindle guide section from the drive unit housing will allow, for example, in application as a surgery instrument for the surgery operation for artificial joint replacement, an exclusive sterilization of the spindle guide section that contacts the interior of a patient's body. On the other hand, as for the drive unit housing that does not contact the interior of a patient's body, a cover or the like will suffice during the surgery. In this way, reduction in the number of parts used in the remote controlled actuator as a whole as well as cost reduction can be achieved.

In the present invention, preferably, the rotary shaft may include an inside-guide-section portion disposed in the spindle guide section and an inside-housing portion disposed in the drive unit housing, and the inside-guide-section portion and the inside-housing portion may be coupled by a coupling so as to be detachable from each other in an axial direction of the rotary shaft and to transmit a rotation about an axis of the rotary shaft. Since the inside-guide-section portion and the inside-housing portion of the rotary shaft are connected with each other by means of the coupling, the rotation of the tool rotation drive source within the drive unit housing can assuredly be transmitted to the spindle guide section even when the guide spindle section and the drive unit housing are detachable from each other.

In the present invention, preferably, the spindle guide section may include an end portion proximal to the drive unit housing, with the end portion being provided with a flange section detachably connected to the drive unit housing. In this case, the connection device may include a plurality of bolts that connect the flange section with the drive unit housing.

Alternatively, the drive unit housing may include a surface, that faces the spindle guide section, formed with an annular protrusion, and the annular protrusion may have an inner periphery to which the flange section is mated and an outer periphery having a threaded portion. In this case, the connection device may include a nut member having a bottom portion provided with an opening in the center portion thereof, into which opening the spindle guide section is inserted, and a bottom surface around the opening for abutment to an end surface of the flange section that faces away from the drive unit housing. The nut member may be threadingly mounted onto the threaded portion so as to connect the flange section with the drive unit housing.

The flange section provided at the spindle guide will facilitate the detachment between the spindle guide section and the drive unit housing, resulting in enhanced connection/detachment operability. In particular, the use of the bolts or the nut member to connect the flange section with the drive unit housing will result in more enhanced connection/detachment operability and will also provide a simplified but inexpensive structure.

In the present invention, preferably, a phase alignment mechanism may be provided for aligning phases of the spindle guide section and of the drive unit housing about an axis of the rotary shaft with each other, and the phase alignment mechanism may be disposed at a connecting portion where the spindle guide section and the drive unit housing are connected.

Such a phase alignment mechanism will facilitate the alignment of the phase of the attitude altering member about the axis of the rotary shaft relative to the drive unit housing, enabling smooth advancement and retraction of the attitude altering member. Also, when the connection device may include a thread mechanism by which the spindle guide section and the drive unit housing are connected on rotating them relative to each other about the axis of the rotary shaft, the alignment of the phase of the spindle guide section relative to the drive unit housing can be facilitated, resulting in an enhanced connection/detachment operability.

In the present invention, preferably, the spindle guide section and the drive unit housing may define a space therebetween filled with a pressurized air, and the space may form a pressurized region with a pressure higher than that of inside of the spindle guide section and higher than that of inside of the drive unit housing.

The pressurized region formed between the spindle guide section and the drive unit housing will prevent coolant liquids and lubricants used in the spindle guide section from entering into the drive unit housing. Configuring the space at a connection or a connecting portion, where the base end of the spindle guide section and the drive unit housing are connected, such that it forms a pressurized region will not need to provide additional spaces for a pressurized region, resulting in a simplified structure.

Where a bearing is provided for rotatably supporting the rotary shaft within the spindle guide section, preferably, a cooling unit may be provided for cooling the bearing with a coolant liquid flowing inside the spindle guide section.

Component parts including, for example, the spindle for rotating the tool and the rotary shaft emit heat by the effect of friction taking place during rotation thereof. The emitting heat so evolved results in heating of the bearing. The use of the cooling unit is effective to cool the bearing and a heated site of those component parts with the coolant liquid. If the coolant liquid is allowed to flow through the inside of the spindle guide section, the spindle guide section can be simplified and downsized with no need to employ any extra tube for the supply of the coolant liquid.

In addition, an effect to lubricate the bearing with the coolant liquid is appreciated. If the coolant liquid is concurrently used for lubrication of the bearing, there is no need to use such a grease or the like as generally employed in the standard bearings and, yet, there is no need to use an extra lubricating device.

A cooling unit may be provided for cooling the tool with a coolant liquid flowing inside the spindle guide section or with a coolant liquid supplied from an outside.

During the processing, the tool and the object to be processed tend to emit heat. The use of the cooling unit is effective to cool the tool and the object to be processed with the coolant liquid.

Preferably, the coolant liquid may include water or saline.

Such a coolant liquid that includes water or saline will not give a harmful effect on a biological body when the distal end member is inserted into the biological body to perform some processing.

In the present invention, the spindle guide section may include a curved portion.

Even with such a curved portion at the spindle guide section, the attitude altering member can be advanced or retracted within the guide hole for its flexibility.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 2A is a longitudinal sectional view showing a distal end member and a spindle guide section both employed in the remote controlled actuator of FIG. 1A;

FIG. 2B is a cross sectional view taken along the line IIB-IIB in FIG. 2A;

FIG. 2C is a diagram showing a structure for coupling the distal end member and a rotary shaft together;

FIG. 9A is a longitudinal sectional view showing a distal end member and a spindle guide section, both employed in a remote controlled actuator according to a second preferred embodiment of the present invention;

FIG. 9B is a cross sectional view taken along the line IXB-IXB in FIG. 9A;

FIG. 10A is a longitudinal sectional view showing a distal end member and a spindle guide section, both employed in a remote controlled actuator according to a third preferred embodiment of the present invention;

FIG. 10B is a cross sectional view taken along the line XB-XB in FIG. 10A;

FIG. 12A is a longitudinal sectional view showing a distal end member and a spindle guide section, both employed in a remote controlled actuator according to a fourth preferred embodiment of the present invention;

FIG. 12B is a cross sectional view taken along the line XIIB-XIIB in FIG. 12A;

FIG. 13A is a longitudinal sectional view showing a distal end member and a spindle guide section, both employed in a remote controlled actuator according to a fifth preferred embodiment of the present invention;

FIG. 13B is a cross sectional view taken along the line XIIIB-XIIIB in FIG. 13A;

FIG. 13C is a view of the housing of the distal end member, as seen from the base end thereof;

FIG. 14A is a longitudinal sectional view showing a distal end member and a spindle guide section, both employed in a remote controlled actuator according to a sixth preferred embodiment of the present invention; and FIG. 14B is a cross sectional view taken along the line XIVB-XIVB in FIG. 14A.

DESCRIPTION OF EMBODIMENTS

Figure 1A:
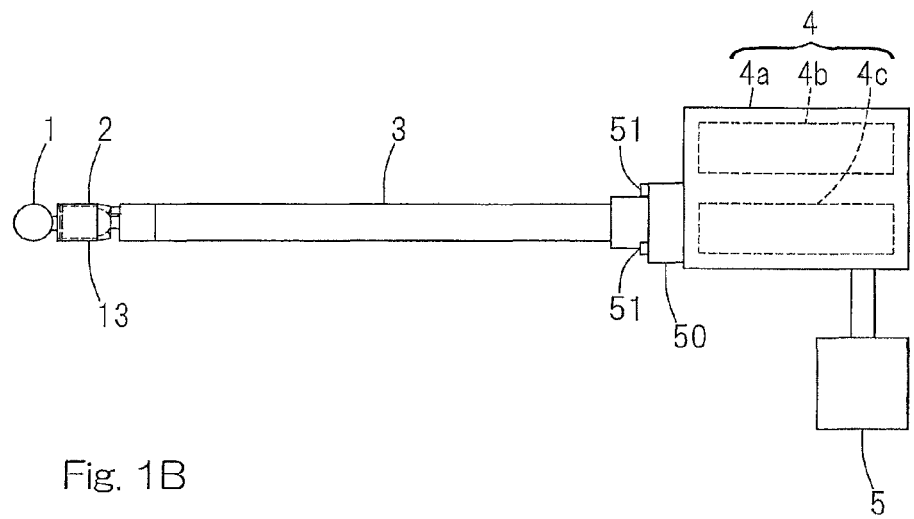
FIG. 1A is a diagram showing a schematic structure of a remote controlled actuator according to a first preferred embodiment of the present invention.
Figure 1B:
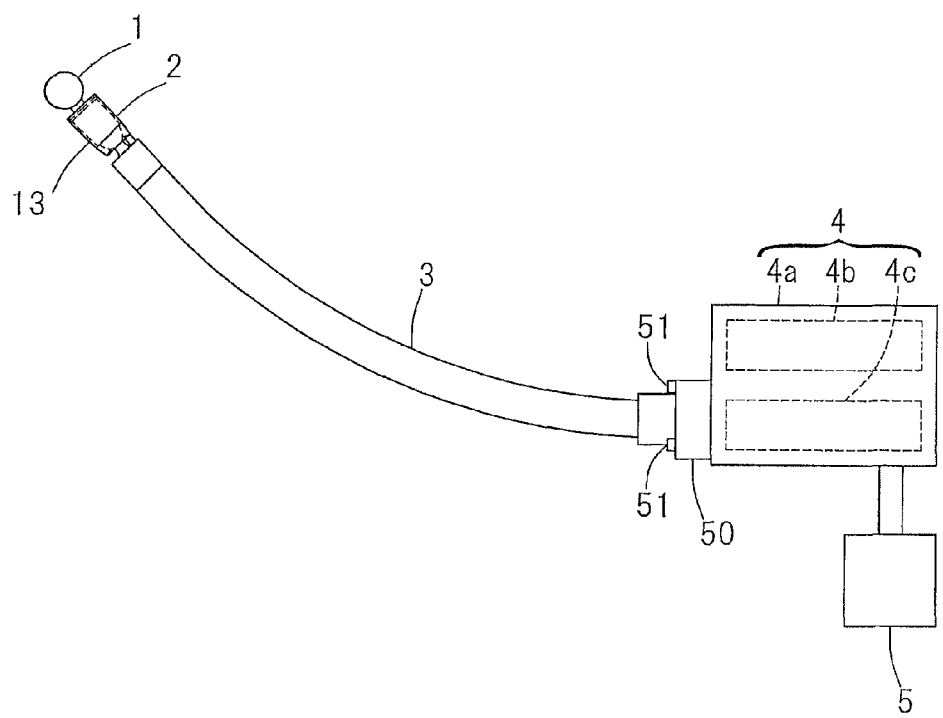
FIG. 1B is a diagram showing a schematic structure of a remote controlled actuator according to a first preferred embodiment of the present invention, in which the remote controlled actuator includes a spindle guide section with a shape different from the one in FIG. 1A.

A first preferred embodiment of the present invention will now be described with particular reference to FIG. 1A to FIG. 5D. Referring to FIGS. 1A and 1B, a remote controlled actuator according to the first embodiment of the present invention includes a distal end member 2 for holding a rotary tool 1, a spindle guide section 3 of an elongated configuration having a distal end to which the distal end member 2 is coupled for displacement in attitude, a drive unit housing 4a to which a proximal end of the spindle guide section 3 is connected, and a controller 5 for controlling a tool rotating drive mechanism 4b and an attitude altering drive mechanism 4c, both accommodated within the drive unit housing 4a. The drive unit housing 4a cooperates with the built-in tool rotating drive mechanism 4b and attitude altering drive mechanism 4c to form a drive unit 4. The drive unit housing 4a is detachably connected to a proximal, base end of the spindle guide section 3 by one or more bolts 51, which functions as a connection device. FIGS. 1A and 1B show the remote controlled actuator with respective spindle guide sections 3 of different configurations.

FIG. 2A is a longitudinal sectional view showing the distal end member 2 and the spindle guide section 3. The distal end member 2 includes a generally or substantially cylindrical housing 11 and a spindle 13 rotatably accommodated within such cylindrical housing 11 through a pair of bearings 12. The spindle 13 is of a tubular shape having a distal side opening and has a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member coupling unit 15. The distal end member coupling unit 15 supports the distal end member 2 for displacement in attitude and is comprised of a spherical bearing. More specifically, the distal end member coupling unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered.

The spindle guide section 3 includes a rotary shaft 22 for transmitting a rotational force exerted by a tool rotating drive source 41 (FIGS. 3A and 3B) accommodated within the drive unit housing 4a. In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 2C, the spindle 13 and the rotary shaft 22 are coupled together by means of a universal joint 23 for transmitting rotation from the rotary shaft 22 to the spindle 13. The universal joint 23 is made up of a groove 13a, defined in a closed base end of the spindle 13, and of a projection 22a defined in a distal end of the rotary shaft 22 and engageable in the groove 13a. The center of joint between the groove 13a and the projection 22a is located at the same position as the centers of curvature O of the guide faces F1 and F2. It is, however, to be noted that the rotary shaft 22 and the projection 22a may be formed of members separate from each other.

The spindle guide section 3 includes an outer shell pipe 25 which forms an outer shell for the spindle guide section 3. The outer shell pipe 25 has a hollow extending to opposite ends thereof, which hollow is made up of a round hole portion 24a at a center portion thereof and three grooved portions 24b radially outwardly depressed from respective circumferential locations of an outer periphery of the round hole portion 24a, which locations form a 120° phase relative to each other, as shown in FIG. 2B. A peripheral wall of a tip end of each of those grooved portions 24b represents a semicircular shape in section. By way of example, the outer shell pipe 25 has an outer diameter within the range of 8 to 10 mm and, also, an inner diameter at a location other than the grooved portions 24b that is within the range of 3 to 5 mm. Also, as material for the outer shell pipe 25, stainless steel or titanium or the like is suitably used.

Since the outer shell pipe 25 is chosen to have such a sectional shape as shown and described above, the wall thickness t of the outer shell pipe 25 at the location other than the grooved portions 24b can be increased. Accordingly, the geometric moment of inertia of the outer shell pipe 25 can be rendered to be ½ or more of a solid shaft of the same outer diameter. For example, in the case of the solid shaft of 8 mm in outer diameter made of a stainless steel material, the geometric moment of inertia is about 200 mm$^4$.

The rotary shaft 22 is arranged within the round hole portion 24a of the hollow 24. The rotary shaft 22 so positioned is rotatably supported by a plurality of rolling bearings 26 positioned spaced a distant apart from each other in a direction axially of the spindle guide section 3, as shown in FIG. 2A. Between the neighboring rolling bearings 26, spring elements 27A for generating a preload on the inner rings of the corresponding rolling bearing 26 and spring elements 27B for generating the preload on the outer rings of the corresponding rolling bearings 26 are alternately disposed relative to each other. Those spring elements 27A and 27B may be employed in the form of, for example, compression springs. The constraint member 21 referred to previously is fixed to a pipe end portion 25a of the outer shell pipe 25 by means of a fixing pin 28 and has its distal end inner peripheral portion supporting a distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

The grooved portions 24b of the hollow 24 are provided with a hollow guide pipe 30 extending to opposite ends thereof. Within a guide hole 30a which is an inner diametric hole of this guide pipe 30, an attitude altering or operating member 31 is reciprocally movably inserted. In the instance as shown, the attitude altering member 31 is in the form of a wire 31a and pillar shaped pins 31b connected to a tip end of the wire 31a. The attitude altering member 31 has a tip end representing a spherical shape which is held in contact with a bottom face of a radial groove portion 11b formed in a base (or proximal) end face of the housing 11. The radial groove portion 11b of the housing 11 is rendered to be an inclined face having its outer diametric side closer to the side of the spindle guide section 3. The other of the pillar shaped pins 31b that is closer to the drive unit housing 4a also has a tip end representing a spherical shape which is held in contact with a lateral surface of a pivot lever 43b (FIG. 3A) which will be explained in detail later.

Figure 3A:
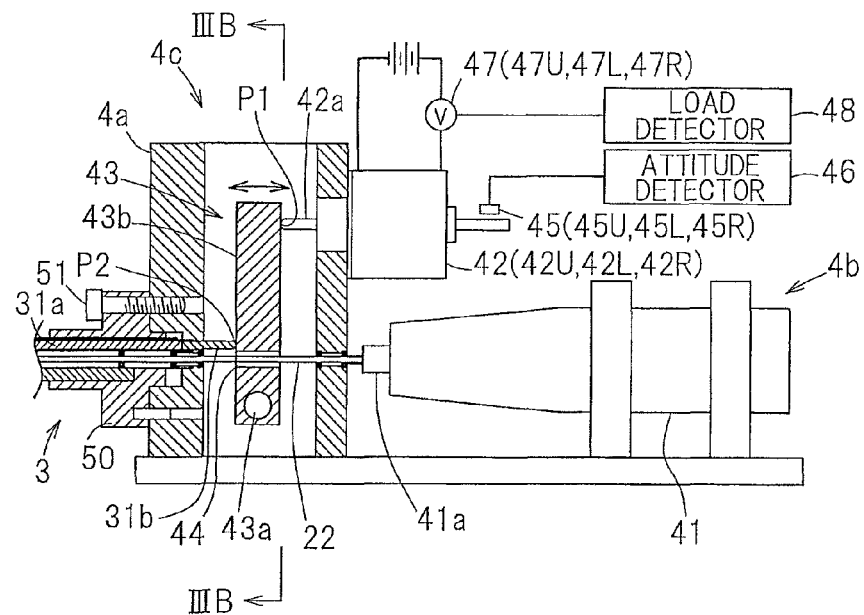
FIG. 3A is a cross sectional view of a tool rotating drive mechanism and an attitude altering drive mechanism of the remote controlled actuator.
Figure 3B:
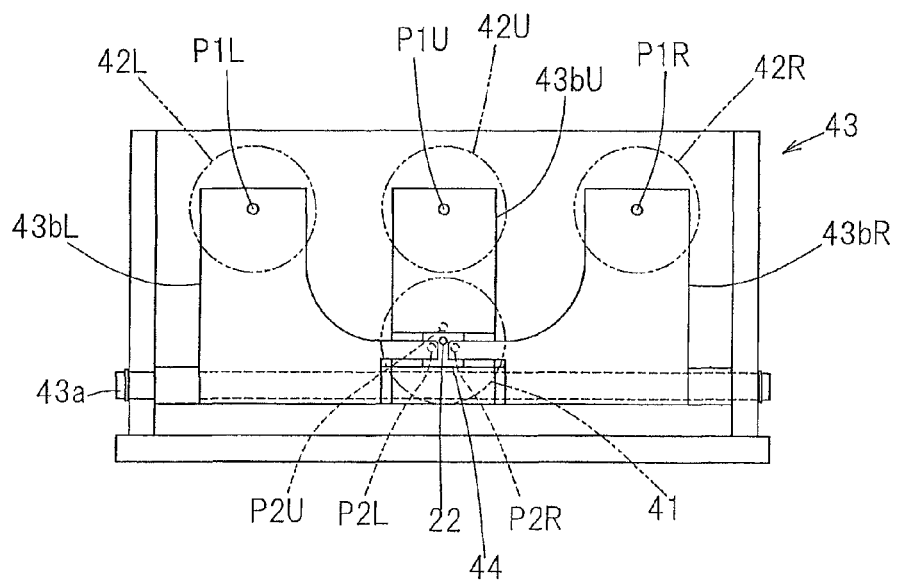
FIG. 3B is a cross sectional view taken along the line IIIB-IIIB in FIG. 3A.

The tool rotating drive mechanism 4b and the attitude altering drive mechanism 4c, both housed within the drive unit housing 4a, are best shown in FIGS. 3A and 3B. The tool rotating drive mechanism 4b makes use of a tool rotating drive source 41. This tool rotating drive source 41 is in the form of, for example, an electric motor, having its output shaft 41a coupled with a base end or proximal end of the rotary shaft 22. The rotary shaft 22 extends through an opening 44 defined in the pivot lever 43b which will be explained in detail later.

The attitude altering drive mechanism 4c makes use of three attitude altering drive sources 42 (42U, 42L, 42R) that are associated, respectively, with the attitude altering members 31 (31U, 31L, 31R) such as shown in FIG. 2B. The attitude altering drive sources 42 may be in the form of, for example, electrically operated linear actuator having an output rod 42a, the movement of the output rod 42a in one of leftward and rightward directions on the drawing plane of FIG. 3A one at a time being transmitted to the corresponding attitude altering member 31 through a force increasing and transmitting mechanism 43. The force increasing and transmitting mechanism 43 includes pivot levers 43b (43bU, 43bL, 43bR) pivotable about a support pin 43a and is so designed and so configured as to allow a force of the output rods 42a to work on a working point P1 of the levers 43b, which are respectively spaced a long distance from the support pin 43a, and as to apply a force to the attitude altering members 31 at a force point P2, which are spaced a short distance from the support pin 43a, wherefore the outputs of the attitude altering drive sources 42 can be increased and then transmitted to the attitude altering members 31. Since the use of the force increasing and transmitting mechanism 43 is effective to enable a large force to be applied to the attitude altering members 31 even in the linear actuator of a low output capability, the linear actuator can be downsized. The attitude altering drive sources 42 may be rotary motors. Alternatively, instead of the use of linear actuators or the like, the attitude of the distal end member 2 may be manually operated from a remote site by remote control.

The attitude altering drive mechanism 4c is provided with operating amount detectors 45 (45U, 45L, 45R) for detecting the operating amount of the corresponding attitude altering drive sources 42 (42U, 42L, 42R) independent of each other. The detection values outputted from these operating amount detectors 45 are outputted to an attitude detector 46. The attitude detector 46 is operable to detect the attitude inclined about the X-axis and Y-axis (FIG. 2B) of the distal end member 2. The attitude detector 46 includes a relation setting unit (not shown), in which the relation between the output signal of the operating amount detector 45 and the attitude of the distal end member 2 inclined is set in terms of an arithmetic equation or table, and makes use of the relation setting means to detect the inclination in attitude in reference to the output signal inputted. This attitude detector 46 may be provided either in the controller 5 (FIG. 1A) or in an external control device.

Also, the attitude altering drive mechanism 4c is provided with supply power meters 47 (47U, 47L, 47R) for detecting the electric energy supplied to the corresponding attitude altering drive sources 42 (42U, 42L, 42R), which are electrically operated actuators, independent of each other. The detection values of these supply power meters 47 are outputted to a load detector 48. This load detector 48 in turn detects a load acting on the distal end member 2 in reference to the outputs of the supply power meters 47. This load detector 48 includes a relation setting unit (not shown), in which the relation between the load and the output signal of the supply power meter 47 is set in terms of an arithmetic equation or table, and makes use of the relation setting unit to detect the load in reference to the output signal so inputted. This load detector 48 may be provided either in the controller 5 (FIG. 1A) or in an external control device.

The controller 5 (FIG. 1A) referred to above is operable to control the tool rotation drive sources 41 and the attitude altering drive sources 42, based on the respective detection values outputted by the attitude detector 46 and the load detector 48.

Figure 4:
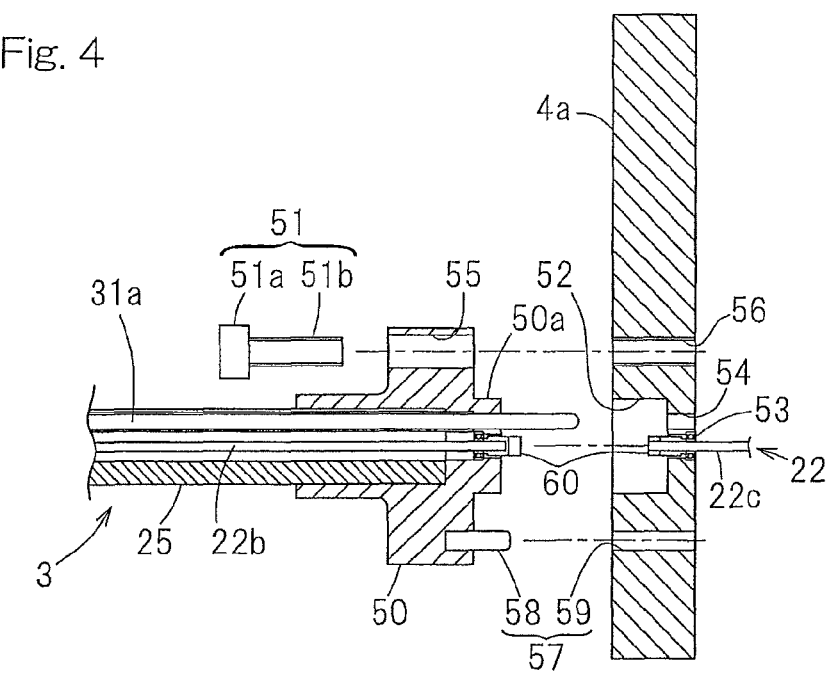
FIG. 4 is a cross sectional view of the connection between the spindle guide section and a drive unit housing of the remote controlled actuator, with the connection being disassembled.
Figure 5A:
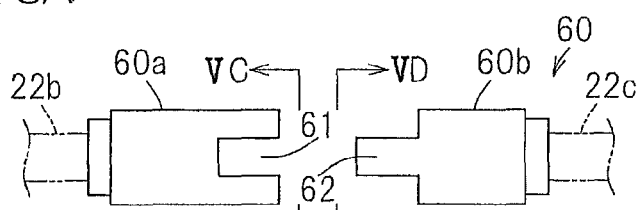
FIG. 5A is a top view showing a coupling in the remote controlled actuator.
Figure 5B:
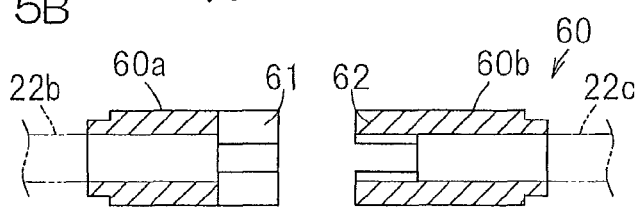
FIG. 5B is a cut-away side view of the coupling.
Figure 5C:
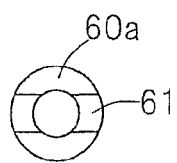
FIG. 5C is a fragmentary view taken in the direction of an arrow VC-VC in FIG. 5A.
Figure 5D:
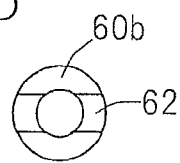
FIG. 5D is a fragmentary view taken in the direction of an arrow VD-VD in FIG. 5A.

FIG. 4 shows the structure of the connection between the spindle guide section 3 and the drive unit housing 4, with the connection being disassembled. As shown in FIG. 4, the base end of the spindle guide section 3 is provided integrally with a flange section 50, to which the drive unit housing 4a is connected by means of a plurality of bolts 51 which function as a connection device. More specifically, the flange section 50 includes one base end surface, confronting the drive unit housing 4a, formed with a protrusion 50a in the center portion thereof. The flange section 50 is connected with the drive unit housing 4a by fitting the protrusion 50a to a cavity 52 formed in the drive unit housing 4a. The cavity 52 includes a bottom portion formed with a central through hole 53 that penetrates through the bottom portion to the other side and that is adapted for the insertion of the rotary shaft 22 and also includes eccentric through holes 54 for the insertion of the respective attitude altering members 31. The plurality of bolts 51 are distributed in a circumferential direction of the flange section 50 and each of the bolts 51 has a head 51a and a shank 51b with the head 51a being in contact with the other surface of the flange section 50 facing away from the drive unit housing 4a and the shank 51b being inserted in a bolt insertion hole 55 of the flange section 50 to screw onto the corresponding threaded hole 56 formed in the drive unit housing 4a. Although, in the illustrated example, the flange section 50 is a member separate from the outer shell pipe 25 of the spindle guide section 3, the flange section 50 may be formed in one-piece or integrally with the outer shell pipe 25.

At a connection or a connecting portion where the rotary shaft 3 and the drive unit housing 4a are connected with each other, a phase alignment mechanism 57 is provided for aligning the phase of the attitude altering member 31 on the side of the spindle guide section 3 and the phase of the holes 54 on the side of the drive unit housing 4a about an axis defined by the rotary shaft 22. The phase alignment mechanism 57 includes a phase alignment pin 58 that protrudes from the base end surface of the flange section 50 and a corresponding phase alignment hole 59 formed in the drive unit housing 4a to which the tip end of the phase alignment pin is adapted to be inserted.

The rotary shaft 22 includes an inside-guide-section portion 22b disposed in the spindle guide section 3 and an inside-housing portion 22c disposed in the drive unit housing 4a.

The inside-guide-section portion 22b and the inside-housing portion 22c are coupled by a coupling 60 so as to be detachable from each other in an axial direction of the rotary shaft 22 and to transmit a rotation about an axis of the rotary shaft 22. As shown in FIGS. 5A to 5D, the coupling 60 includes a guide-section-side coupling body 60a fixedly mounted to the axial end of the inside-guide-section portion 22b of the rotary shaft 22 and a housing-side-coupling body 60b fixedly mounted to the axial end of the inside-housing portion 22c of the rotary shaft 22. Fixation between the inside-guide-section portion 22b and the guide-section-side coupling body 60a and fixation between the inside-housing portion 22c and the housing-side-coupling body 60b may be performed, for example, by press-fitting. The guide-section-side coupling body 60a includes an end surface, confronting the housing-side-coupling body 60b, formed with an engagement groove 61 therein, while the housing-side-coupling body 60b includes an end surface, confronting the guide-section-side-coupling body 60a, formed with an engagement protrusion 62. The engagement between the engagement groove 61 and the engagement protrusion 62 with the spindle guide section 3 and the drive unit housing 4a being connected with each other allows the transmission of rotation from the housing-side-coupling body 60b to the guide-section-side-coupling body 60a.

The operation of the remote controlled actuator of the construction hereinabove described will now be described in detail.

When the tool rotating drive source 41 as shown in FIG. 3A is driven, the rotational force thereof is transmitted to the spindle 13 through the rotary shaft 22 to thereby rotate the tool 1 together with the spindle 13. The load acting on the distal end member 2 when the tool 1 then being rotated cuts a bone or the like is detected from the detection value of the supply power meter 47 by the load detector 48. Accordingly, when the amount of feed of the remote controlled actuator in its entirety and the alteration of attitude of the distal end member 2, as will be described later, are controlled in dependence on the value of the load detected in the manner described above, cutting of the bone can be properly carried out while the load acting on the distal end member 2 is maintained properly.

During operation, the three attitude altering drive sources 42 (42U, 42L, 42R) such as shown in FIG. 3B are driven for the cooperative advancement and retraction of the respective attitude altering members 31 (31U, 31L, 31R) such as shown in FIG. 2B, to drive the distal end member 2 to alter the attitude thereof.

By way of example, when one of the attitude altering members 31U is advanced towards the distal, tip end side while the other two attitude altering members 31L and 31R are retracted, the housing 11 for the distal end member 2 is pressed by the upper attitude altering member 31U to allow the distal end member 2 to be altered in attitude along the guide surfaces F1 and F2 with the distal, tip end side consequently oriented downwardly as viewed in FIG. 2A. At this time, those attitude altering drive sources 42 are controlled so that the amount of advance or retraction of each of the attitude altering members 31 may become proper. On the other hand, when each of those attitude altering members 31 is retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 2A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 2A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased.

Since the base end face 11b of the housing 11 of the distal end member 2 is rendered to be an inclined face having its outer diametric side closer to the side of the spindle guide section 3, the base end face 11b of the housing 11 can be easily slid relative to the attitude altering members 31 when the attitude altering members 31 are pressing the base end face 11b of the housing 11, resulting in a smooth attitude alteration of the housing 11.

Since the attitude altering member 31 is inserted through the guide hole 30a of the guide pipe 30, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is made up of a wire and has a flexible property, the attitude altering operation of the distal end member 2 is carried out accurately even when the spindle guide section 3 is curved. In addition, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

The remote controlled actuator of the foregoing construction is utilized in grinding the femoral marrow cavity during, for example, the artificial joint replacement surgery and during the surgery, it is used with the distal end member 2 in its entirety or a part thereof inserted into the body of a patient. Because of this, with such distal end member 2 as described above that can be altered in attitude by remote control, the bone can be processed in a condition with the tool 1 maintained in a proper attitude at all times and the opening for insertion of the artificial joint can be finished accurately and precisely.

Since the spindle guide section 3 of the elongated shape includes the rotary shaft 22 provided in the center portion of the outer shell pipe 25 as shown in FIG. 2B, and the guide pipes 30, in which the respective attitude altering members 31 are accommodated, while the guide pipes 30 are arranged around the rotary shaft 22 so as to be juxtaposed in the circumferential locations spaced 120° in phase from each other, the arrangement balance of the rotary shaft 22 and the guide pipes 30 is improved. Since the outer shell pipe 25 has a large wall thickness at its principal portion other than the grooved portions 24b, the rigidity (geometric moment of inertia) of the spindle guide section 3 is high. For this reason, not only can the positioning accuracy of the distal end member 2 be increased, but the cutting capability can also be increased. Also, since the guide pipes 30 are arranged in the respective grooved portions 24b, positioning of the guide pipes 30 in the circumferential direction can be facilitated, resulting in a good assemblability.

As shown in FIG. 2A, since the outer diametric surfaces of the rolling bearings 26 supporting the rotary shaft 22 are supported by the guide pipes 30, the outer diametric surfaces of the rolling bearings 26 can be supported with no need to use any extra member. Also, since the preload is applied to the rolling bearings 26 by means of the spring elements 27A and 27B, the rotary shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

The detachable connection between the spindle guide section 3 and the drive unit housing 4a by means of the connection device in the form of bolts 51 will allow the selective mounting of spindle guide sections 3 with various configurations as shown in FIGS. 1A and 1B for good conformation to the shape of the object to be cut. Furthermore, the easy detachment of the spindle guide section 3 from the drive unit housing 4a will allow, for example, in application as a surgery instrument for the surgery operation for artificial joint replacement, an exclusive sterilization of the spindle guide section 3 that contacts the interior of a patient's body. On the other hand, as for the drive unit housing 4a that does not contact the interior of a patient's body, a cover or the like will suffice during the surgery. In this way, reduction in the number of parts used in the remote controlled actuator as a whole as well as cost reduction can be achieved.

Especially, in this first preferred embodiment, the flange section 50 provided at the base end of the spindle guide section 3 will facilitate the detachment between the spindle guide section 3 and the drive unit housing 4a, resulting in an enhanced connection/detachment operability. Also, the use of bolts 51 as the connection device will result in more enhanced connection/detachment operability and will also provide a simplified but inexpensive structure.

It is desirable to prepare a plurality of spindle guide sections 3 of various configurations including, in addition to those of straight configurations, those of curved configurations with different degrees of curves. The spindle guide section 3 may be of a configuration having a uniform radius of curvature throughout its extension or may be of a configuration partially having a radius of curvature different from the rest of its extension. Alternatively, the spindle guide section 3 may be of a configuration having a partially curved portion. For the spindle guide section 3 of a curved configuration, the outer shell pipe 25, the guide pipe 30 and a reinforcement shaft 34 (as shown in, for example, FIGS. 9A and 9B) also need to be of a curved configuration. Also, the material for the rotary shaft 22 is preferably an easily deformable material, such as shape-memory alloys.

Figure 6:
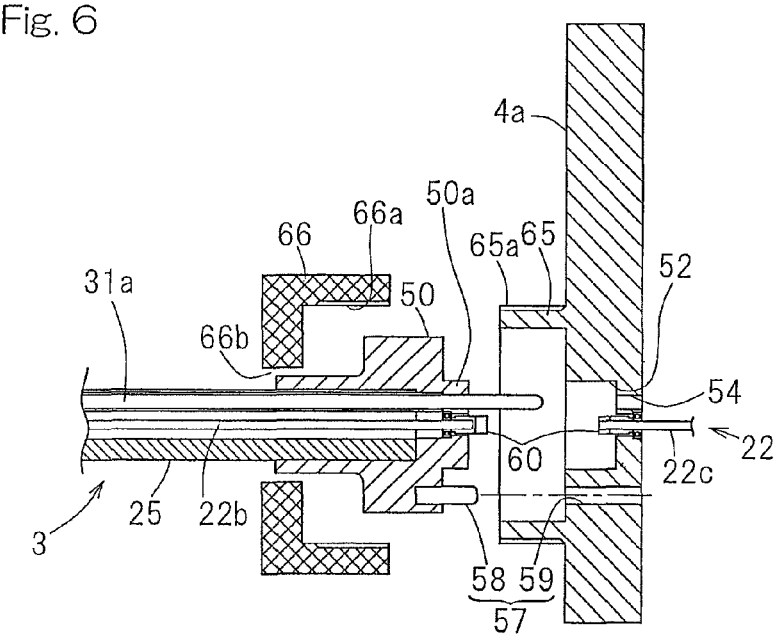
FIG. 6 is a cross sectional view of the connection between the spindle guide section and a drive unit housing of another remote controlled actuator, with the connection being disassembled.

FIG. 6 shows an alternative construction of the connection between the spindle guide section 3 and the drive unit housing 4a, with the spindle guide section 3 and the drive unit housing 4a being disconnected. Similar to the above described construction, the connection in FIG. 6 also includes the flange section 50 provided in the tip end of the spindle guide section 3 with the protrusion 50a of the flange section 50 mated to the cavity 52 of the drive unit housing 4a. The drive unit housing 4a includes a surface, confronting the spindle guide section 3, formed with an annular protrusion 65. The annular protrusion 65 has an inner periphery surface to which the flange section 50 is adapted to be fitted and an outer peripheral surface formed with a first threaded portion 65a onto which a second threaded portion 66a formed on the connection device in the form of a nut member 66 is threadingly mounted so as to achieve a connection between the flange section 50 and the drive unit housing 4a. The nut member 66 is in the form of a cap nut and includes a bottom portion having an opening or a through hole 66b in the center portion thereof and an annular side wall having the second threaded portion 66a on an inner periphery thereof. The spindle guide section 3 is inserted into the opening 66b, with a bottom surface around the opening 66b in abutment with an end surface of the flange section 50 that may face away from the drive unit housing 4a. The nut member 66 is tightened through the first and second threaded portions 65a and 66a so as to connect the flange section 50 to the drive unit housing 4a. In this way, the flange section 50 is fixedly sandwiched between the nut member 66 and the drive unit housing 4a. The connection in FIG. 6 will also result in an enhanced detachment/connection operability of the spindle guide section 3 relative to the drive unit housing 4a and will also provide a simplified but inexpensive structure.

Figure 7:
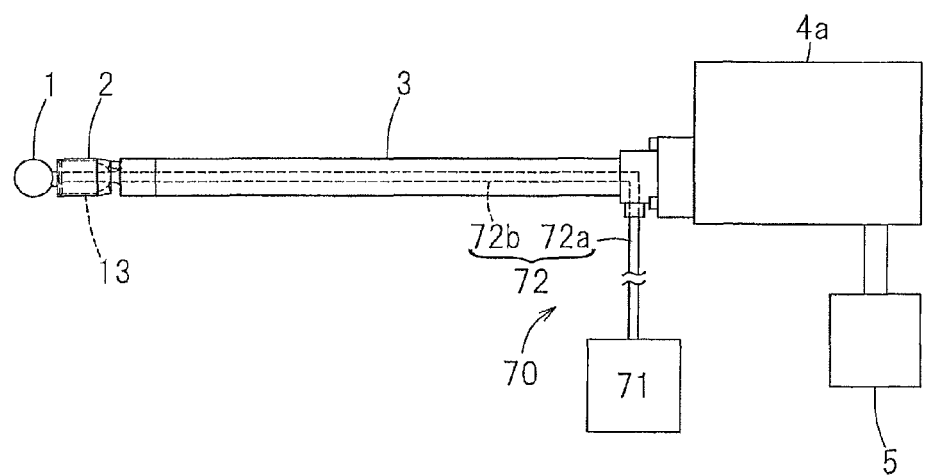
FIG. 7 is a schematic diagram showing a remote controlled actuator with a cooling unit.

In view of the spindle guide section 3 being of a hollow shape, a remote controlled actuator of the present invention can be provided with a cooling unit 70 for cooling the tool 1 or the like such as shown in FIG. 7. In other words, the cooling unit 70 includes a coolant liquid supply device 71 provided outside the remote controlled actuator and a coolant liquid supply passage or tube 72 for supplying a coolant liquid, fed from the coolant liquid supply device 71, towards the tip end side through the interiors of the spindle guide section 3 and the distal end member 2 and is capable of discharging the coolant liquid from a tip end of the distal end member 2 towards the tool 1 in the axial direction. The coolant liquid supply passage 72 is made up of an outer passage portion 72a, extending from the coolant liquid supply device 71 to the spindle guide section 3, and an inner passage portion 72b extending through the interiors of the spindle guide section 3 and the distal end member 2, and in the inner passage portion 72b, the outer shell pipe 25 (FIGS. 2A and 2B) of the spindle guide section 3 and the housing 11 (FIG. 2A) for the distal end member 2 form the coolant liquid supply passage 72.

When the coolant liquid flows through the interiors of the spindle guide section 3 and the distal end member 2, the rotary shaft 22, the rolling bearings 26 and 29 and the spindle 13 are cooled. Those rotatable members tend to emit heat under the influence of friction occurring during the rotation. Also, by the action of the coolant liquid discharged from the distal end member 2, the tool 1 and an article to be processed are cooled. In this way, as a result of the flow of the coolant liquid through the interiors of the spindle guide section 3 and the distal end member 2, there is no need to provide the outside with any tube for the supply of the coolant liquid, and therefore, the spindle guide section 3 and the distal end member 2 can be simplified and downsized. In case that the amount of the coolant liquid flowing through the outer shell pipe 25 is not sufficient, further coolant liquids may be supplied from the outside to cool the tool 1 and/or the article to be processed. It is to be noted that the coolant liquid may be concurrently used for lubrication of the rolling bearings 26 and 29. By so doing, there is no need to use any grease or the like that is generally utilized in bearings and, moreover, there is no need to employ an extra lubricating device.

The liquid coolant referred to above is preferably in the form of water or physiological saline. If the liquid coolant is employed in the form of water or physiological saline, the liquid coolant will bring no adverse influence on the living body when the processing is performed with the distal end member 2 inserted into the living body. Where water or physiological saline is employed for the liquid coolant, component parts, with which the liquid coolant contacts, are preferably made of stainless steel that is excellent in resistance to corrosion. Any other component parts forming the remote controlled actuator may be made of stainless steel.

Figure 8:
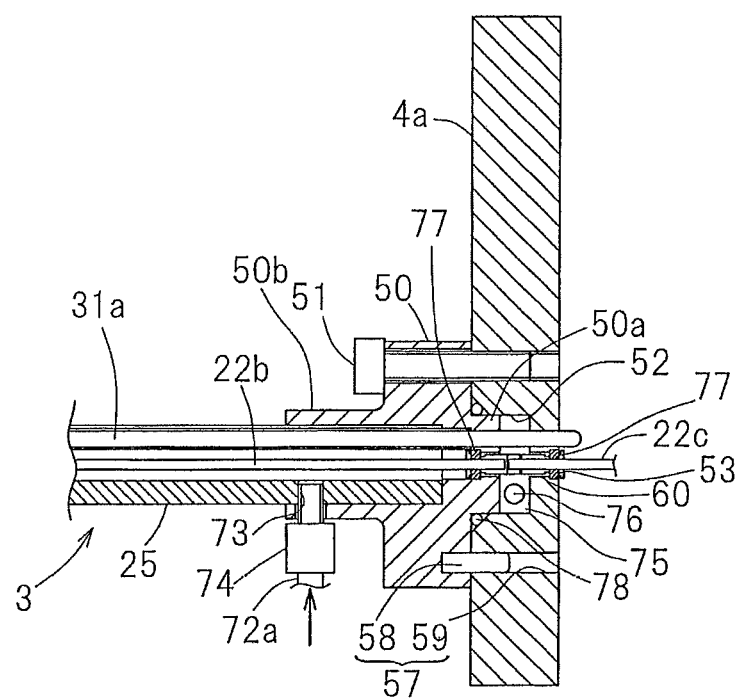
FIG. 8 is a cross sectional view of the connection between the spindle guide section and a drive unit housing of the remote controlled actuator.

The coolant unit 70 may be provided by configuring the connection between the spindle guide section 3 and the drive unit housing 4a such as shown in FIG. 8. In other words, in the connection as shown in FIG. 4, a coolant liquid feed hole 73 is provided in a thin-thickness section 50b of the flange section 50 to connect the interior of the spindle guide section 3 to the outside, and the coolant liquid feed hole 73 is coupled with the outer passage portion 72a of the coolant liquid supply passage 72 through a pipe joint 74. In this way, the coolant liquid is fed from the outer passage portion 72a of the coolant liquid supply passage 72 to the spindle guide section 3 in such a manner as indicated by an arrow illustrated in FIG. 8.

When the protrusion 50a of the flange section 50 is fitted to the cavity 52 of the drive unit housing 4a, a space 75 unoccupied by the protrusion 50a is formed inside the cavity 52. In other words, the space 75 is formed at the connection between the spindle guide section 3 and the drive unit housing 4a. A pressurized air feed hole 76 is provided to feed a pressurized air into the space 75. A hole formed in the flange section 50 to which the inside-guide-section portion 22b of the rotary shaft 22 is inserted and the central through hole 53 to which the inside-housing portion 22c of the rotary shaft 22 is inserted are sealed by respective seal members 77. The respective seal members 77 may be, for example, sliding-contact bearings supporting the inside-guide-section portion 22b and the inside-housing portion 22c of the rotary shaft 22, respectively. An O-ring 78 is disposed between a base portion of the protrusion 50a of the flange section 50 and an open end portion of the cavity 52 of the drive unit housing 4a. By feeding a pressurized air from the outside to the space 75 through the pressurized air feed hole 76 by means of, for example, a pump, the space 75 forms a pressurized region with a pressure higher than that of inside of the spindle guide section 3 and higher than that of inside of the drive unit housing 4a.

The pressurized region formed between the spindle guide section 3 and the drive unit housing 4a will prevent coolant liquids used in the spindle guide section 3 from entering into the drive unit housing 4a. Configuring the space 75 at the connection or the connecting portion, where the base end of the spindle guide section 3 and the drive unit housing 4a are connected, such that it forms a pressurized region will eliminate the need to provide additional spaces for a pressurized region, resulting in a simplified structure.

FIGS. 9A and 9B show a second preferred embodiment of the present invention. A remote controlled actuator of this embodiment includes differ from the first preferred embodiment as shown in FIG. 2 in that the outer shell pipe 25 of the spindle guide section 3 has a uniform thickness. Within this outer shell pipe 25, three guide pipes 30 are provided at respective circumferential locations spaced 120° in phase from each other and the attitude altering members 31 are inserted within the guide hole 30a, each of which is an inner diametric hole of each of the guide pipes 30, for advancement and retraction. Between those three guide pipes 30, a plurality of reinforcement shafts 34 are arranged on the same pitch circle diameter C as that of the guide pipes 30 in an alternate manner. The reinforcement shafts 34 are non-hollow, solid shafts that ensure the rigidity of the spindle guide section 3. The reinforcement shafts 34 along with the guide pipes 30 are in contact with the inner diametric surface of the outer shell pipe 25 and the outer diametric surfaces of the rolling bearings 26 to support the diametric surfaces of the rolling bearings 26. As for other features, the second preferred embodiment is the same as the first preferred embodiment.

FIGS. 10A and 10B show a third preferred embodiment of the present invention. A remote controlled actuator of this embodiment include a single guide pipe 30 between the inner diametric surface of the outer shell pipe 25 of the spindle guide section 3 and the rotary shaft 22 and the guide pipe 30 has an inner diametric hole functioning as a guide hole 30a within which an attitude altering member 31 is inserted for advancement and retraction. A plurality of reinforcement shafts 34 similar to the second embodiment described above are disposed, together with the guide pipe 30, in the same pitch circle diameter C. Between a base end face of the housing 11 of the distal end member 2 and a tip end face of the outer shell pipe 25 of the spindle guide section 3, a restoring elastic member 32 made of, for example, a compression coil spring, is arranged at a location spaced 180° degrees circumferentially in phase from the circumferential location where the attitude altering member 31 is positioned. The restoring elastic member 32 biases the distal end member 2 towards a predetermined attitude. The guide faces F1 and F2 are spherical surfaces each having the center of curvature lying at the point O or cylindrical surfaces each having a lateral X-axis as a longitudinal axis passing through the point O. As for other features, the third preferred embodiment is the same as the first preferred embodiment.

Figure 11A:
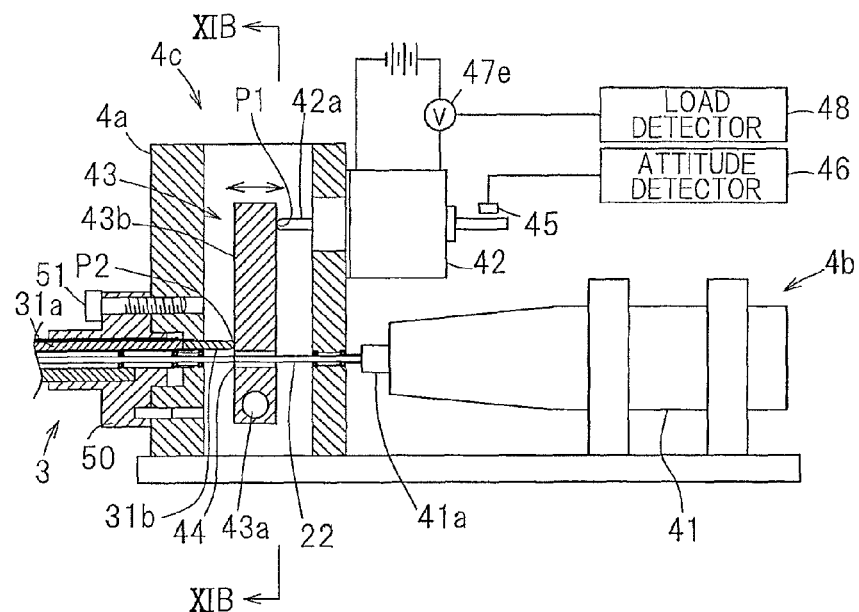
FIG. 11A is a cross sectional view of a tool rotating drive mechanism and an attitude altering drive mechanism of the remote controlled actuator.
Figure 11B:
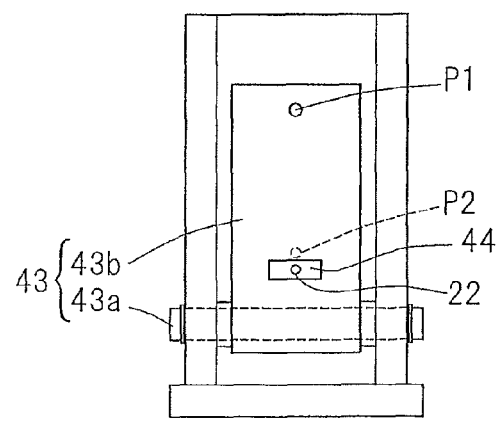
FIG. 11B is a cross sectional view taken along the line XIB-XIB in FIG. 11A.

FIGS. 11A and 11B show a tool rotating drive mechanism 4b and an attitude altering drive mechanism 4c for the remote controlled actuator according to the third embodiment. The attitude altering drive mechanism 4c includes a single altering drive source 42 and the force increasing and transmitting mechanism 43 has a configuration for a single attitude altering member 31. The tool rotating drive mechanism 4b has the same configuration as that shown in FIGS. 3A and 3B.

The alteration of the distal end member 2 in attitude may be performed as described below. By way of example, if the attitude altering member 31 is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 10A. If the attitude altering member 31 is conversely retracted by the attitude altering drive source 42, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 10A. At this time, a pressure from the attitude altering member 31, the elastic repulsive force from the restoring elastic member 32 and a reactive force from the constraint member 21 are applied to the distal end member coupling unit 15 and, depending on the balance of those applied forces, the attitude of the distal end member 2 is determined. The attitude of the distal end member 2 is detected by the attitude detector 46 from the detection value of the operating amount detector 45. For this reason, the attitude of the distal end member 2 can be properly controlled by remote control.

FIGS. 12A and 12B illustrate a fourth preferred embodiment of the present invention. The remote controlled actuator according to this fourth embodiment includes two guide pipes 30 spaced 180 degrees in phase relative to each other within an outer shell pipe 25 and each of the guide pipes 30 has an inner diametric hole functioning as a guide hole 30a within which an attitude altering member 31 is inserted for advancement and retraction. Between those two guide pipes 30, a plurality of reinforcement shafts 34 are arranged on the same pitch circle diameter C as that of the guide pipes 30. No restoring elastic member 32 is provided. The guide faces F1 and F2 are spherical surfaces each having the center of curvature lying at the point O or cylindrical surfaces each having a lateral X-axis as a longitudinal axis passing through the point O.

The drive unit 4 (not shown) is provided with two attitude altering drive sources 42 (not shown) for selectively advancing and retracting respective attitude altering members 31 so that when those two attitude altering drive sources 42 are driven in respective directions opposite to each other, the distal end member 2 can be altered in attitude. By way of example, when the upper attitude altering member 31 shown in FIG. 12A is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards. Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 12A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces. According to this construction, since the housing 11 for the distal end member 2 is pressed by the two attitude altering members 31, as compared with the previously described embodiment in which it is pressed by a single attitude altering member 31, the attitude stability of the distal end member 2 can be increased.

FIGS. 13A to 13C illustrate a fifth preferred embodiment of the present invention. The remote controlled actuator according to this fifth embodiment is such that the base end face 11b (FIG. 13C) of the housing 11 for the distal end member 2 is formed with a radial groove portion 11c (as best shown in FIG. 13C) and the spherical tip end of the attitude altering member 31 is held in contact with a bottom face of the radial groove portion 11c. This radial groove portion 11c cooperates with the attitude altering member 31 to form a rotation preventing mechanism 37 and, accordingly, when the tip end portion of the attitude altering member 31, then inserted into the radial groove portion 11c, contacts a side face of the radial groove portion 11c, the distal end member 2 can be prevented from rotating about the center line CL of the spindle 13 relative to the spindle guide section 3.

Such a rotation preventing mechanism 37 will prevent, even when the distal end member 2 holding the tool 1 becomes out of control due to, for example, a failure in the attitude altering drive mechanism 4c (FIG. 11A) or a controller for the mechanism 4c, rotation of the distal end member 2 about the center line CL that may unintentionally damage the vicinity of the location to be worked and prevent the fracture in the distal end member 2 itself. It should be noted that FIG. 13A shows an example in which the remote controlled actuator includes a single attitude altering member 31, but the above discussion equally applies to cases in which the remote controlled actuator includes a plurality of attitude altering members 31.

In the aforementioned embodiments, the base end face 11b of the housing 11 for the distal end member 2, where an attitude altering member 31 contacts, is rendered to be an inclined face having its outer diametric side closer to the side of the spindle guide section 3, and the inclined face has a straight shape in cross section. Alternatively, however, the inclined face may have a curved shape in cross section such as in a sixth preferred embodiment shown in FIGS. 14A and 14B, for example, an arcuate shape. Possibly, the base end face 11b of the housing 11 for the distal end member 2 may be rendered to be a face extending perpendicular to the direction of advancement/retraction of the attitude altering member 31, instead of the aforementioned inclined face. It should be noted that FIGS. 14A and 14B show an example in which the remote controlled actuator includes the single attitude altering member 31, but the above discussion equally applies to cases in which the remote controlled actuator includes a plurality of attitude altering members 31.

Although in the aforementioned embodiments, the attitude altering member 31 includes the wire 31a and the pillar shaped pin 31b provided at the opposite ends of the wire 31a, the attitude altering member 31 may be constituted solely by a single wire 31a with the pillar shaped pin 31b dispensed with. Furthermore, the attitude altering member 31 may be constituted by, instead of such a wire 31a, a plurality of juxtaposed pillar members or spherical members, each of which is relatively short in length along a longitudinal direction of the attitude altering member 31.

Although the present invention has been fully described as applied to the remote controlled actuator for medical use, the present invention can be equally applied to the remote controlled actuator for any other use than the medical use. By way of example, if it is designed for use in machine processing, drilling to form a curved hole and cutting at a site deep into the groove can be accomplished.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

DESCRIPTION OF REFERENCE NUMERALS

| | |
|---|---|
| 1: | Tool |
| 2: | Distal end member |
| 3: | Spindle guide section |
| 4a: | Drive unit housing |
| 5: | Controller |
| 13: | Spindle |
| 15: | Distal end member connecting unit |
| 22: | Rotary shaft |
| 22a: | Projection |
| 22b: | Inside-guide-section portion |
| 22c: | Inside-housing portion |
| 26, 29: | Rolling bearing |
| 30: | Guide pipe |
| 30a: | Guide hole |
| 31: | Attitude altering member |
| 41: | Tool rotating drive source |
| 42: | Attitude altering drive source |
| 50: | Flange section |
| 51: | Bolt (Connection device) |
| 57: | Phase alignment mechanism |
| 60: | Coupling |
| 65: | Annular protrusion |
| 66: | Nut member |
| 66b: | Opening |
| 70: | Cooling unit |
| 75: | Space |

What is claimed is:

1. A remote controlled actuator comprising:
a drive unit housing including a tool rotating drive source;
a spindle guide section of an elongated configuration, a base end of the spindle guide section being connected to the drive unit housing; and
a distal end member fitted to the spindle guide section through a distal end member connecting unit for alteration in attitude,
wherein the distal end member rotatably supports a spindle for holding a tool;
the spindle guide section includes a rotary shaft for transmitting rotation of the tool rotating drive source to the spindle, a guide hole extending to opposite ends of the spindle guide section, and an attitude altering member reciprocally movably inserted within the guide hole for altering the attitude of the distal end member;
the attitude altering member includes a tip end held in contact with the distal end member which is configured to selectively advance or retract;
an attitude altering drive source for selectively advancing or retracting the attitude altering member is provided within the drive unit housing;
a connection device is provided for detachably connecting the spindle guide section with the drive unit housing; and
a space is formed between the spindle guide section and the drive unit housing, the space being configured to be filled with a pressurized air and form a pressurized region with a pressure higher than that of inside of the spindle guide section and higher than that of inside of the drive unit housing, the space including a pressurized air feed hole configured to feed the pressurized air into the space,
wherein the spindle guide section includes an end portion proximal to the drive unit housing, the end portion being provided with a flange section detachably connected to the drive unit housing, the flange section having a protrusion,
the protrusion of the flange section is fitted to a cavity provided in the drive unit housing.

2. The remote controlled actuator as claimed in claim 1, wherein the rotary shaft includes an inside-guide-section portion disposed in the spindle guide section and an inside-housing portion disposed in the drive unit housing, and
the inside-guide-section portion and the inside-housing portion are coupled by a coupling so as to be detachable from each other in an axial direction of the rotary shaft and to transmit a rotation about an axis of the rotary shaft.

3. The remote controlled actuator as claimed in claim 1, wherein
an empty space inside the cavity, unoccupied by the protrusion, defines the space forming the pressurized region.

4. The remote controlled actuator as claimed in claim 3, wherein the connection device includes a plurality of bolts that connect the flange section with the drive unit housing.

5. The remote controlled actuator as claimed in claim 3, wherein the drive unit housing includes a surface, that faces the spindle guide section, formed with an annular protrusion,
the annular protrusion has an inner periphery to which the flange section is mated and an outer periphery having a threaded portion, and
the connection device includes a nut member having a bottom portion provided with an opening in the center portion thereof, into which opening the spindle guide section is inserted, and a bottom surface around the opening for abutment to an end surface of the flange section that faces away from the drive unit housing, the nut member being threadingly mounted onto the threaded portion so as to connect the flange section with the drive unit housing.

6. The remote controlled actuator as claimed in claim 1, further comprising a phase alignment mechanism for aligning phases of the spindle guide section and of the drive unit housing about an axis of the rotary shaft with each other, the phase alignment mechanism being disposed at a connecting portion where the spindle guide section and the drive unit housing are connected.

7. The remote controlled actuator as claimed in claim 1, further comprising:
a bearing for rotatably supporting the rotary shaft within the spindle guide section; and
a cooling unit provided for cooling the bearing with a coolant liquid flowing inside the spindle guide section.

8. The remote controlled actuator as claimed in claim 1, further comprising a cooling unit for cooling the tool with a coolant liquid flowing inside the spindle guide section or with a coolant liquid supplied from an outside.

9. The remote controlled actuator as claimed in claim 7, wherein the coolant liquid includes water or saline.

10. The remote controlled actuator as claimed in claim 8, wherein the coolant liquid includes water or saline.

11. The remote controlled actuator as claimed in claim 1, wherein the spindle guide section includes a curved portion.

* * * * *

UNITED STATES PATENT AND TRADEMARK OFFICE
CERTIFICATE OF CORRECTION

PATENT NO.        : 8,794,100 B2
APPLICATION NO.   : 14/045387
DATED             : August 5, 2014
INVENTOR(S)       : Hiroshi Isobe et al.

It is certified that error appears in the above-identified patent and that said Letters Patent is hereby corrected as shown below:

In the Specification

Column 1, Line 11, After "priority to" delete "a-".

Signed and Sealed this
Twenty-fourth Day of February, 2015

Michelle K. Lee
*Deputy Director of the United States Patent and Trademark Office*